United States Patent [19]

De Boer

[11] Patent Number: 4,772,555
[45] Date of Patent: Sep. 20, 1988

[54] DEDICATED RIBOSOMES AND THEIR USE

[75] Inventor: Herman A. De Boer, Granada, Calif.

[73] Assignee: Genentech, Inc., South San Francisco, Calif.

[21] Appl. No.: 716,781

[22] Filed: Mar. 27, 1985

[51] Int. Cl.$^4$ .................. C12P 21/00; C12N 15/00; C12N 1/20; C07H 15/12
[52] U.S. Cl. .................. 435/68; 435/91; 435/172.3; 435/253; 435/320; 536/27; 935/10; 935/3; 935/29; 935/45
[58] Field of Search .................. 536/27; 435/253, 68, 435/172.3; 935/45

[56] References Cited

U.S. PATENT DOCUMENTS 4,582,800 4/1986 Crowl .................. 435/70

OTHER PUBLICATIONS

Stark et al., *J. Mol. Biol.* 159: 417–439, 1982.
Steitz, J. A., "Genetic Signals +Nucleotide Sequences in Messenger RNA" in Biological Regulation +Dev., Goldberger, R. F. (Ed.) vol. 1, 349–399 (1979).
Kozak, M. "Microbiological Reviews" 47(1): 1–45, (Mar. 1983).
De Boer, H. A. et al., "DNA" 2(3): 231–235 (1983).
De Boer, H. A. et al., "Biochem. Soc. Symp," 48:233–244, (1983).
Stark, M. J. R. et al., "J. Mol. Biol." 178: 303–322, (1984).
Van Charldorp et al., "Nucl. Acids Res." 10(4): 1149–1158 (1982).

*Primary Examiner*—Thomas G. Wiseman
*Assistant Examiner*—Thomas D. Mays

[57] ABSTRACT

A method is described that dedicates specialized ribosomes to the synthesis of desired proteins. DNA which encodes rRNA having a mutant anti-Shine-Dalgarno sequence is used to transform a host cell in combination with DNA encoding messsenger RNA for the desired protein having a complementary mutant Shine-Dalgarno sequence. Since the mutant sequences are selected so as to be substantially unrecognized by either endogenous messenger RNA or ribosomes, respectively, the synthesis of protein proceeds in a dedicated system without interference from other host cell protein synthetic machinery.

21 Claims, 9 Drawing Sheets

```
        Pribnow box      +1      SDIX              start
        TAGTTTAATGTGTGGAAGCTTTCCTCCTCTAGaattctatg___HGH
        ATCAAATTACACACCTTCGAAAGGAGGAGATCttaagatac
   (ΔHpaI)                                 EcoRI Pribnow box      +1      SDX               start
        TAGTTTAATGTGTGGAAGCTTTGTGTGTCTAGaattctatg___HGH
        ATCAAATTACACACCTTCGAAACACACAGATCttaagatac
   (ΔHpaI)                                 EcoRI
```

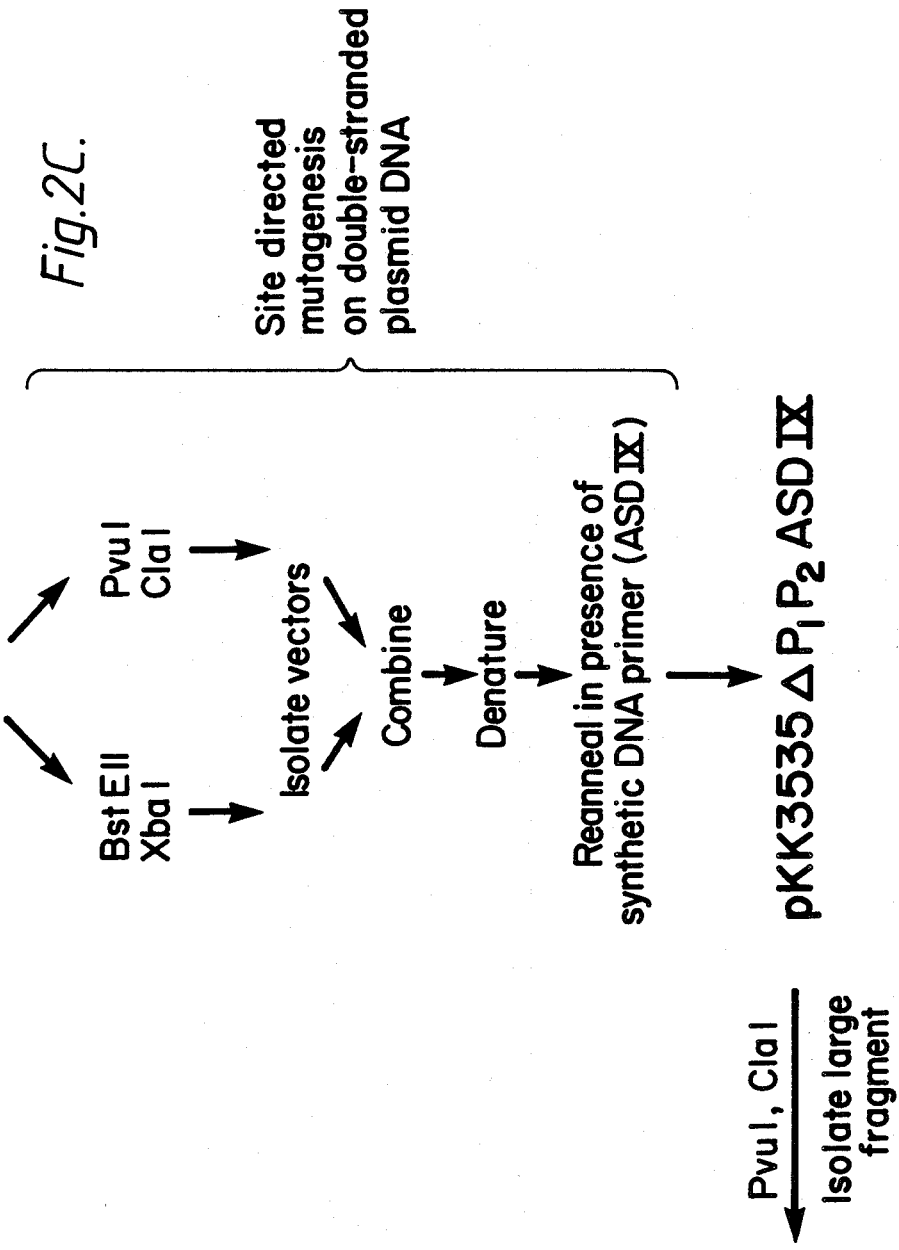

DEDICATED RIBOSOMES AND THEIR USE

This relates to the field of protein synthesis. In particular, it is concerned with harnessing elements of cellular protein synthesis to the specialized production of a preselected protein.

The initiation of protein synthesis in vivo is a complex cascade of events which are only now beginning to be understood, notwithstanding that it has been over ten years since Shine and Dalgarno noted that the start codon of *E. coli* messenger RNA (mRNA) is preceded by a nucleotide sequence complementary to a sequence found very close to the 3' end of the 16S ribosomal RNA (16S rRNA). This sequence, which has since become known as the Shine-Dalgarno (SD) sequence, is GGAGG (read from left to right as the 5' to 3' direction). It should be understood, however, that this is a consensus sequence representing the most frequently encountered nucleotides. Accordingly, the term SD sequence shall be used to refer to the consensus SD sequence as well as the SD sequences in other ribosome mRNA binding sites. Other SD sequences recognized by *E. coli* ribosomes include AGGAGGU, GAGGA, GGGGU, UGGGU, GAGGU, UGAGGA, UAAGGA, GGA, AGGU, GAGGU, AGGAGG, UAAGGAGGU, GGUGAU, AGGAGU, AGGA, GAGGUGAU, AGGAG, AAGGAG, GGAG, GGU, GAG, AGG, AGGA, GGUGGU, UGGAG, and UAAGAA (F. Goldberger et al., 1979, *Biological Regulation and Development*, Vol. 1, pp. 349-399). While SD sequences exhibit substantial variability, they are characterized in part by the absence of cytosine and the ability to form base paired complexes with RNA in a region in the 3' terminus of 16S rRNA. This region in the rRNA will be referred to as the anti-SD (ASD) sequence. The 3' terminal nucleotide sequence of 16S rRNA proximal to the ASD sequence is highly conserved among bacteria, yeast and eukaryotes (Van Charldorp et al., 1982, "Nucleic Acids Research" 10(4): 1149-1158), and among bacteria is highly conserved throughout. For example, the 16S rRNA 3' termini for *E. coli* and *P. Vulgaris* are both UCACCUCCUUA$_{OH}$, for *B. stearothermophilis*, UCACCUCCUUUCUA$_{OH}$, and for Synechococcus, UCACCUCCUUU$_{OH}$. Note that the ASD CCUCC is the complementary to the SD consensus sequence GGAGG. Nonetheless, the well-conserved ASD sequence also is capable of participating in the initiation of translation from mRNAs having the various SD sequences described above.

SD sequences are believed to function as follows: Preceding the initiation of translation, the 30S ribosomal subunit binds via its structural RNA (16S rRNA) to the SD sequence on the messenger RNA. It is believed that this binding brings the 30S particle in the right position for binding of the fMet-tRNA to the ATG in the so-called P-site of the 30S particle. After these events the 50S ribosomal subunit binds to form the 70S ribosomal particle. At this point protein initiation is completed and the elongation phase begins.

The translational efficiency of mRNA in bacteria differs by several orders of magnitude. Although the parameters that affect translation efficiency are poorly understood, the nature of the SD sequence has been shown to be one of them. This knowledge has been derived from a study of fortuitous or predetermined, site-directed mutations in SD sequences. For example, a mutation is known that improves the potential for base pairing of mRNA with the 16S rRNA and which also enhances the translational efficiency. However, another mutation which reduced SD-ASD complementarily between mRNA and rRNA from 8 to 4 bases did not affect translation efficiency, perhaps because the residual 4 bases were in the most favorable position for interaction with 16S rRNA. For a review of such mutations see Kozak, "Microbiological Reviews" 47(1): 1-45 (1983).

Further, it is known that an increase in SD-ASD complementarity between mRNA and rRNA from 4 bases to 13 bases, achieved through the use of a portable SD region, reduced the translational efficiency about two-fold (de Boer et al., 1983, "Biochem. Soc. Symp." 48: 233-244). It also now is known that the bases immediately following the Shine-Dalgarno sequence affect the translation efficiency (Kozak, op cit). A or T residues affect translation positively, whereas G residues (and C residues to a lesser extent) reduce translatability severely (de Boer et al., op cit). Also affecting translation efficiency are sequences preceding the start codon (Hui et al., 1984, "The EMBO Journal" 3(3): 623-629). Therefore the effects of mutations in the initiation region remain unpredictable because translation efficiency is clearly not simply a function of mRNA.rRNA complementarity; a screening procedure will be employed to evaluate the effects of the mutations.

It is known to insert site-directed mutations into DNA encoding the central domain of 16S rRNA (Stark et al., 1984, "J. Mol. Biol." 178:303-322). The processing and assembly of transcripts from these mutants was severely impaired; in some instances the mutations completely blocked both processes, while in other cases rRNA maturation and ribosome assembly were retarded.

Present methods for the recombinant synthesis of proteins in cells harness preexisting cellular mechanisms. Typically, vectors such as plasmids are used to transfect host cells. The DNA in these vectors is replicated and transcribed into mRNA by the cellular polymerases, whereafter the mRNA is translated by an endogenous ribosome population that simultaneously is engaged in the synthesis of normal cellular proteins. Since the objective of recombinant protein synthesis is to obtain high yields of a particular desired protein, various techniques have been developed to attempt to force the host cell to focus on synthesis of the desired protein in preference to other host cell proteins. For example, inducible promoters have been linked to DNA encoding heterologous protein to enable one to activate transcription of the DNA by exposure of the cells to an inducing agent. Thus the host cells are permitted to become well established before transcriptional activation of the foreign DNA. This notwithstanding, the new transcripts must compete with host cell mRNA for a limited ribosome population which, in *E. coli*, is about 250,000 per cell, thereby reducing the translation of the induced transcripts and the resulting yield of desired protein.

A method is needed that will focus the translational machinery of host cells on the synthesis of one particular desired protein, to the exclusion of other normal cell proteins.

In addition, improved methods are needed for optimizing the interaction of ribosome and messenger RNA to achieve maximal translation efficiency in the synthesis of desired proteins in host cells.

Further, methods are needed for modifying the 16S rRNA ASD sequence and its flanking regions in a predetermined fashion.

These and other objects of this invention will be apparent from consideration of this specification as a whole.

SUMMARY

The foregoing objects are achieved by a method which comprises (1) providing at least one vector comprising (a) a DNA sequence encoding 16S rRNA having a mutant ASD sequence; and (b) a DNA sequence encoding a protein and having an untranslated 5' region comprising a mutant SD sequence which is complementary to the mutant 16S rRNA ASD sequence;

(2) transfecting the vector into a host cell; and (3) culturing the host cell to permit expression of the protein.

The key feature is that the mutant 16S rRNA ASD sequence and the mutant mRNA SD sequence are complementary. The mutant 16S rRNA ASD sequence is selected so that, to the maximum extent, it is substantially unable to bind to or initiate protein synthesis from endogenous cellular mRNA, and vice versa. Thus, the ribosomes containing the mutant 16S rRNA ASD sequence in effect are dedicated to the synthesis of the messenger to which they have been tailored.

Ribosomes assembled after the active transcription of DNA encoding the mutant 16S rRNA ASD sequence are believed to be responsible for growth inhibition in host cells. This is ameliorated by placing the mutant rRNA under the control of an inducible promoter in expression systems.

The method herein is facilitated by novel DNA encoding 16S ribosomal RNA which has a predetermined mutation within the last approximately 20 nucleotides at the 3' end of the RNA. This region of the rRNA includes the ASD sequence. More specifically, DNA is provided that encodes 16S ribosomal RNA, the RNA having as its 3' terminus $GGA(N)_aY(N)hd\ b\text{-}OH$, wherein N is a nucleotide, a is an integer of 0 to about 5, b is an integer of 0 to about 10 and Y is an oligoribonucleotide other than CCUCC containing about from 3 to 15 nucleotides. In one embodiment, N(b) is UUA, UUUCUA or UUU.

DNA also is provided that encodes mRNA complementary to the mutant rRNA. This mRNA is unique in that it is cytosine rich, on the order of greater than about 25 mole percent of cytosine nucleotide.

BRIEF DESCRIPTION OF THE DRAWINGS

FIGS. 2A-2E is a schematic illustration of the construction of a vector comprising DNA that encodes a mutant 16S rRNA ASD sequence and complementary mutant mRNA.

DETAILED DESCRIPTION

Figure 1A:
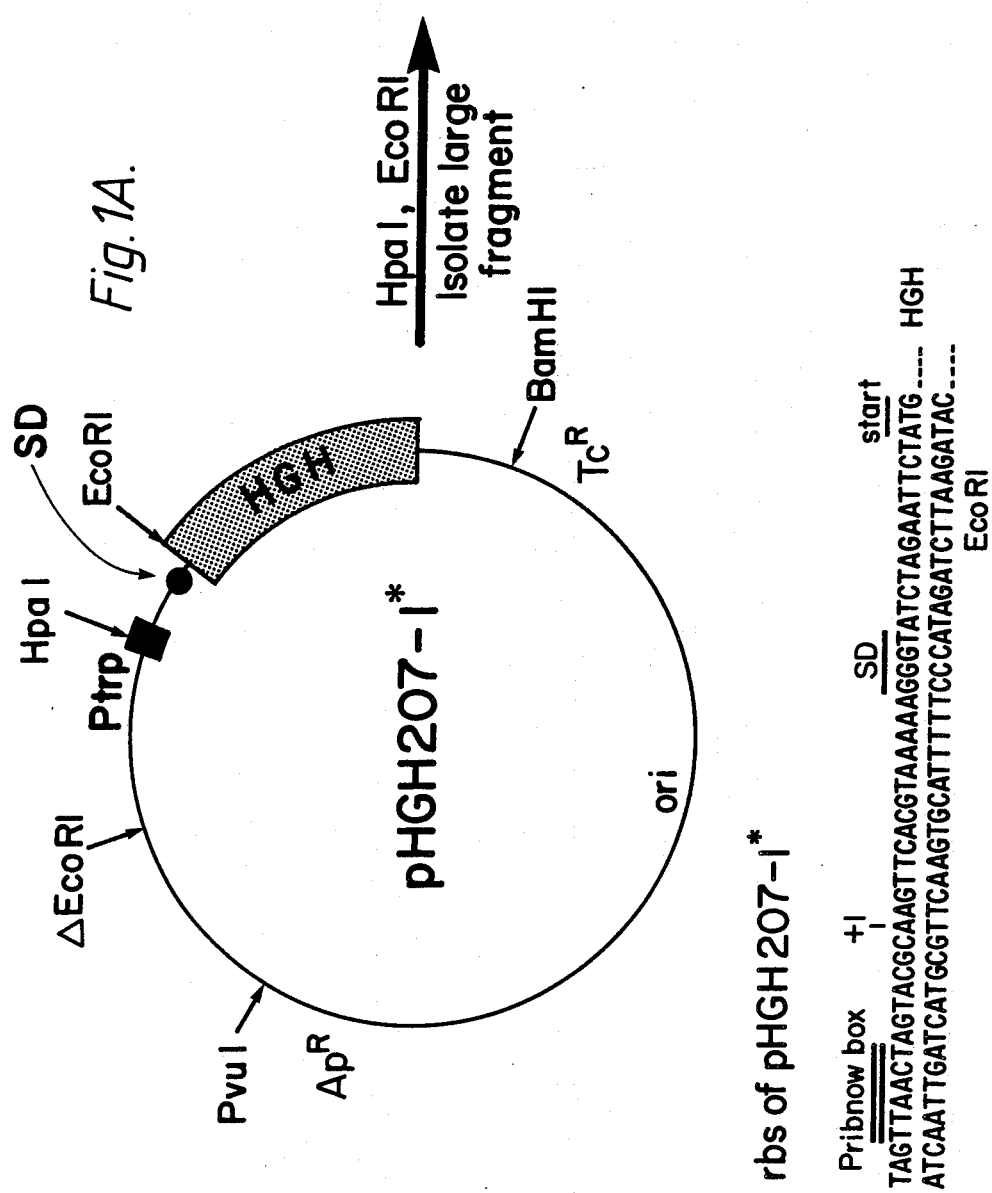
FIGS. 1A-1C depicts the construction of a vector for expressing DNA which encodes mutant mRNA SD sequences.

The DNA encoding the 16S rRNA ASD sequence and that which encodes the mRNA SD sequence are both mutated in order to establish them as complementary to one another. Complementarity is defined traditionally, i.e., RNA sequences are complementary when they are capable of forming heteroduplex complexes by hydrogen bonding. For the purposes herein, G and C, A and U, and G and U are nucleotides that form complementary base pairs, and complementary sequences will contain about from 3 to 7 contiguous complementary nucleotides. It is not necessary, however, for all of the nucleotides in complementary sequences to base pair. Typically, the existence of several internal nucleotides that do not base pair will not prevent the formation of heteroduplexes, particularly if complementarity is permissive with respect to the nucleotides in question, e.g. U with G. It should be understood that the terms Shine-Dalgarno(SD) and anti-Shine-Dalgarno(ASD) sequence are used in their functional rather than the usual compositional sense. In fact, the mutant SD and ASD sequences of this invention are largely the opposite complements of wild-type SD and ASD sequences. However, since the mutants act properly together in initiating protein synthesis they are nonetheless termed SD and ASD sequences.

The complementary mutant rRNA and mRNA SD and ASD sequences are of sufficient length and character to minimize binding to, and protein initiation on, the endogenous host messengers. This is determined by preparing a series of complementary mutants under the control of an inducible promoter as is described infra, transfecting host cells, inducing the mutant 16S rRNAs at the same growth stage and measuring the post-induction growth rates among the transformants. The mutant rRNAs that result in the least growth repression, but which nonetheless remain substantially incapable of participating in the translation of endogenous messengers, are preferred for use herein. Generally, however, the 16S rRNA mutant ASD sequences will contain a large molar percentage of guanine i.e., about from 25 to 100 mole percent of the nucleotides will be guanidine. This distinguishes these mutants from the normal ASD-sequences, which contain no guanine. Of course the complementary mRNA SD sequence will contain an excess of cytosine, again the opposite of the typical messenger initiation sites, on the order of greater than about 25 mole percent cytosine. In effect, in one embodiment the natural mRNA and rRNA ASD and SD sequences are substituted for one another.

The 3' end of the 16S rRNA carries the mutant ASD sequence. The mutant ASD sequence desirably is positioned in the same location as the native sequence. However, the mutant sequences may be longer or shorter than the native sequence (which is typically 5 nucleotides long). The mutant sequences are about from 3 to 15 nucleotides long (of which uncomplementary nucleotides may be present at a ratio of less than about 1 in 5 nucleotides). Preferably, the mutant sequences are about from 4 to 6 nucleotides in length.

It is not necessary that the mutant rRNA and mRNA sequences be substituted precisely at the same location as the native ASD and SD sequences. For example, the gram negative microbial 16S rRNA 3' terminus consensus sequence is $UGGAUCACCUCCUUA_{OH}$, wherein the sequence complementary to the mRNA SD concensus (GGAGG) is underlined. lined. The mutant ASD sequence is preferably a G-rich direct substitution mutant for the 5 ASD nucleotides CCUCC, most preferably GGAGG. However, the CCUCC sequence may be substituted for by a longer or shorter sequence, for example TGGAGG or GGAG. Alternatively, or additionally, the mutant sequence is shifted upstream or downstream, for example to yield UGGAUCGGAGGAUUA$_{OH}$ or UGGAUCAUGGAGGUA$_{OH}$. In all of the foregoing mutants one or more nucleotides from the regions flanking the complementary insert may be deleted, for example as in UGGAUCAGGAGGUA$_{OH}$. Note, however, that when the mutant site is substituted so as to increase or decrease the length of the 3' rRNA downstream from the complementary region, then the number of nucleotides between the complementary mRNA SE sequence and the mRNA start codon also should be adjusted, preferably in the same direction and by the same number of nucleotides. Generally, the 16S rRNA ASD mutants will be located within the last about from 7 to 20 nucleotides of the 3' terminus of the rRNA.

16S rRNA is encoded by 7 genes in *E. coli*, all of which encode the same 3' region. These and 16S rRNA genes from other microbial cells have been identified and are publicly available from the *E. coli* or other cellular genomes. For example, the rrnB rRNA operon (promoter and DNA encoding the rrnB rRNA) has been cloned and sequenced (J. Brosius et al., 1981, "Plasmid" 6: 112–118) and is used as suitable starting material. DNA encoding 16S rRNA, preferably from the intended host cell, is cloned in a replicable vector in conventional fashion (see J. Brosius, op cit). In an alternative embodiment the 16S rRNA chosen is the erythromycin resistant 16S rRNA (Sigmund et al., 1984, "Nucl. Acids Res." 12: 4653–4663). Typically, these vectors then are modified in two ways. First, the 16S rRNA-encoding DNA is placed under the control of an inducible promoter. Then the DNA encoding the ASD sequence (and its flanking regions, if desired) is mutated in the desired fashion in order to create a sequence complementary to the mutant SD sequence to be used with the mRNA.

Inducible promoters are well known and publicly available. Examples include the lambda phage P$_L$, metallothionein, and lac-UV5 promoters that are induced, respectively, by increasing the culture temperature, or by adding copper ions or isopropyl-B-D.thiogalactoside to the culture medium. Other suitable promoters recognizable by the intended host cell will be apparent to the ordinary artisan, e.g. the tac promoter (de Boer et al., in *Genes: Structure and Function* pp. 205-248 (1983). Ordinarily the inducible promoter should be such that the ratio of induced to uninduced promoted RNA should be greater than about 10:1. DNA encoding both the 16S rRNA and the messenger RNA are desirably placed under the control of inducible promoters. The same promoter may be used for both, but ordinarily only the rRNA promoter will need to be inducible.

The starting DNA encoding the desired protein product may be obtained from eukaryotic or prokaryotic sources. The protein need not even be heterogeneous to the host cell. The starting DNA typically is a cDNA including the native 5' untranslated region. Where the cDNA is the reverse transcript of a eukaryotic mRNA, no SD sequence will be present. If this DNA is to be expressed in prokaryotes it is preferred to remove the eukaryotic 5' untranslated region and substitute a prokaryotic 5' sequence, including an SD sequence. This sequence is conveniently supplied by in vitro synthesis or from the gene from which the promoter is obtained. Many prokaryotic 5' regions are known and useful for this purpose. Alternatively, the mutant complementary region is simply substituted for nucleotides in the eukaryotic 5' region at optional spacing from the start codon (about from 5 to 9 nucleotides upstream from the start codon).

The DNA sequences encoding mutant rRNA and mRNA preferably are located on the same vector. This permits selection for transformation by both DNA sequences using a single selection agent, e.g. ampicillin in the case of amp$^r$ gene-bearing vectors. If two vectors are used then two selection agents should be used to ensure cotransformation.

The host cells for use herein preferably are prokaryotes because knowledge relating to the protein initiation systems of prokaryotes is more advanced than in the case of eukaryotes, particularly higher eukaryotic cells such as mammalian cells. Suitable prokaryotes include gram negative organisms such as *E. coli* and Pseudomonas and gram positive microbes such as Bacillus. Nonetheless, the principles of this invention are equally applicable to dedicated expression systems in eukaryotes. For example, the cytoplasmic rRNA of mammalian cells contains the 3' terminal sequence UCAUUA-OH. This sequence is mutated in accord herewith to introduce the prokaryotic anti-Shine-Dalgarno sequence CCUCC so that the mutant rRNA terminates in UCACCUCCUUA-OH. This DNA is then cotransformed into host cells along with DNA encoding mRNA having a complementary sequence located 5' to the start codon of the desired protein and 5' to the start codon of a selection gene, e.g. DHFR. Thus, only cells that take up the transfected DNA and are capable of expressing protein in a dedicated ribosome system will survive the selection.

Where the rRNA containing the mutant ASD is under the control of an inducible promoter the host cell must be able to repress the inducible promoter, e.g. it must be able to synthesize sufficient quantities of a repressor protein. For example, the lac or tac promoter optimally is to be used with host strains known in the art per se which overproduce a lac repressor, e.g. *E. coli* D1210 laci$^g$.

It is not critical that the cell cultures transformed with inducible rRNA be induced at any particular point in the growth cycle, although preferably the cultures are induced as they enter the logarithmic phase. This enables the culture to accumulate sufficient endogenous ribosomes to synthesize for example the ribosomal proteins and polymerases needed to support the dedicated ribosome population. If erythromycin-resistant 16S rRNA is employed, erythromycin should be added to the culture only after a substantial population of dedicated ribosomes has been synthesized.

In order to simplify the Examples certain frequently occurring methods may be referenced by shorthand phrases.

Plasmids are designated by a low case p preceded and/or followed by capital letters and/or numbers. The starting plasmids herein are commercially available, are publically available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes, and the sites for which each is specific is called a restriction site. "Partial" digestion refers to incomplete digestion by a restriction enzyme, i.e., conditions are chosen that result in cleavage of some but not all of the sites for a given restriction endonuclease in a DNA substrate.

The various restriction enzymes used herein are commercially available and their reaction conditions, cofactors and other requirements as established by the enzyme suppliers were used. Restriction enzymes commonly are designated by abbreviations composed of a capital letter followed by other letters and then, generally, a number representing the microorganism from which each restriction enzyme originally was obtained. In general, and unless otherwise provided, about 1 µg of plasmid or DNA fragment is used with about 1 unit of enzyme in about 20 µl of buffer solution. Appropriate buffers and substrate amounts for particular restriction enzymes are specified by the manufacturer. Incubation times of about 1 hour at 37° C. are ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional (T. Maniatis et al., 1982, *Molecular Cloning* pp. 133-134).

"Recovery" or "isolation" of a given fragment of DNA from a restriction digest means separation of the digest on polyacrylamide gel electrophoresis, identification of the fragment of interest by comparison of its mobility versus that of marker DNA fragments of known molecular weight, removal of the gel section containing the desired fragment, and separation of the gel from DNA. This procedure is known generally. For example, see R. Lawn et al., 1981, "Nucleic Acids Res." 9: 6103-6114, and D. Goeddel et al., 1980, "Nucleic Acids Res." 8: 4057.

Southern Analysis is a method by which the presence of DNA sequences in a digest or DNA-containing composition is confirmed by hybridization to a known, labelled oligonucleotide or DNA fragment. For the purposes herein, unless otherwise provided, Southern analysis was used for this purpose and was accomplished by separation of digests on 1 percent agarose, denaturation and transfer to nitrocellulose by the method of E. Southern, 1975, "J. Mol. Biol." 98: 503-517, and hybridization as described by T. Maniatis et al., 1978, "Cell" 15: 687-701.

"Transformation" means introducing DNA into an organism so that the DNA is replicable, either as an extrachromosomal element or chromosomal integrant. Unless otherwise provided, the method used herein for transformation of *E. coli* is the CaCl$_2$ method of Mandel et al., 1970, "J. Mol. Biol." 53: 154.

"Ligation" refers to the process of forming phosphodiester bonds between two double stranded nucleic acid fragments (T. Maniatis et al., Id., p. 146). Unless otherwise provided, ligation may be accomplished using known buffers and conditions with 10 units of T4 DNA ligase ("ligase") per 0.5 µg of approximately equimolar amounts of the DNA fragments to be ligated.

DNA is prepared from transformants by isolating cloned plasmid DNA from microbial culture. Unless otherwise provided, the alkaline/SDS method of Maniatis et al., Id. p. 90., may be used.

"Oligonucleotides" are short length single or double stranded polydeoxynucleotides which are chemically synthesized by known methods and then purified on polyacrylamide gels.

All literature citations are expressly incorporated by reference.

The following examples should be considered illustrative of the invention and not limiting thereof.

EXAMPLE 1

Figure 1B:
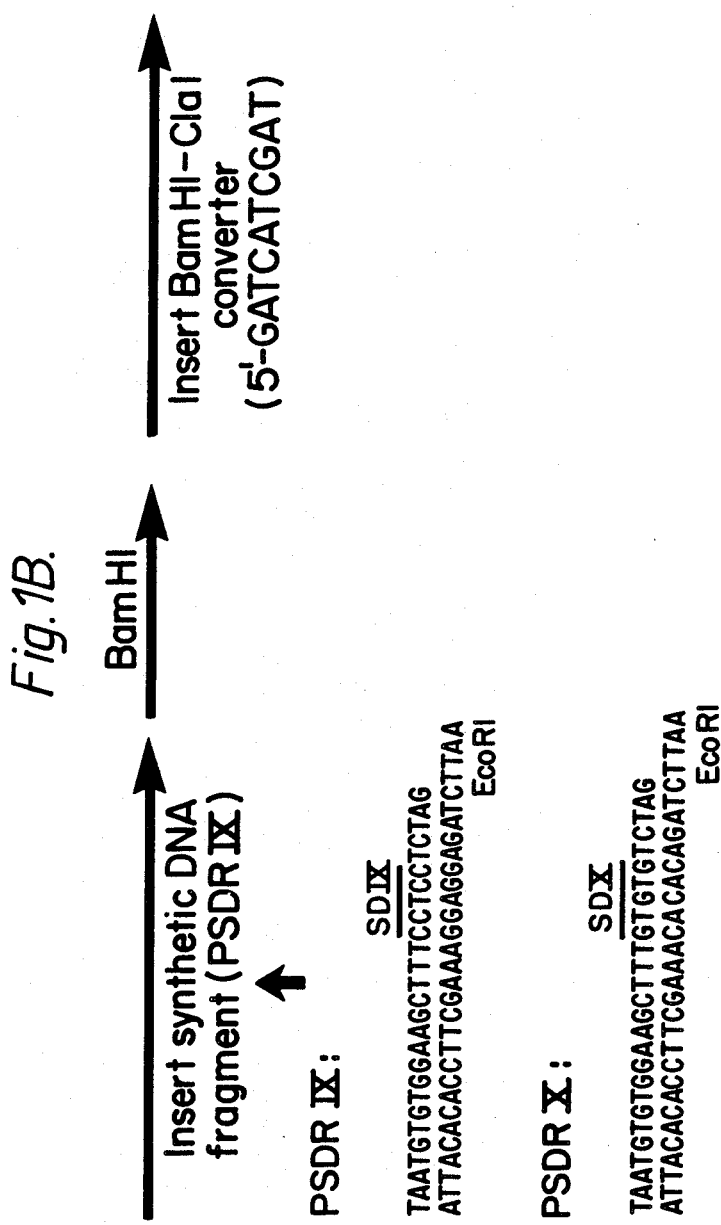
Figure 1C:
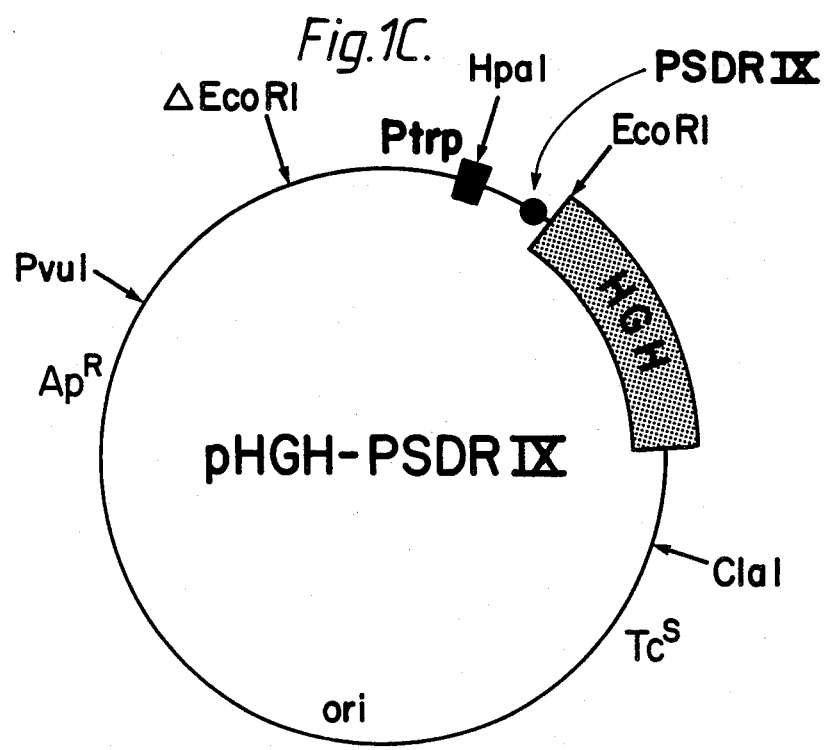
Figure 2A:
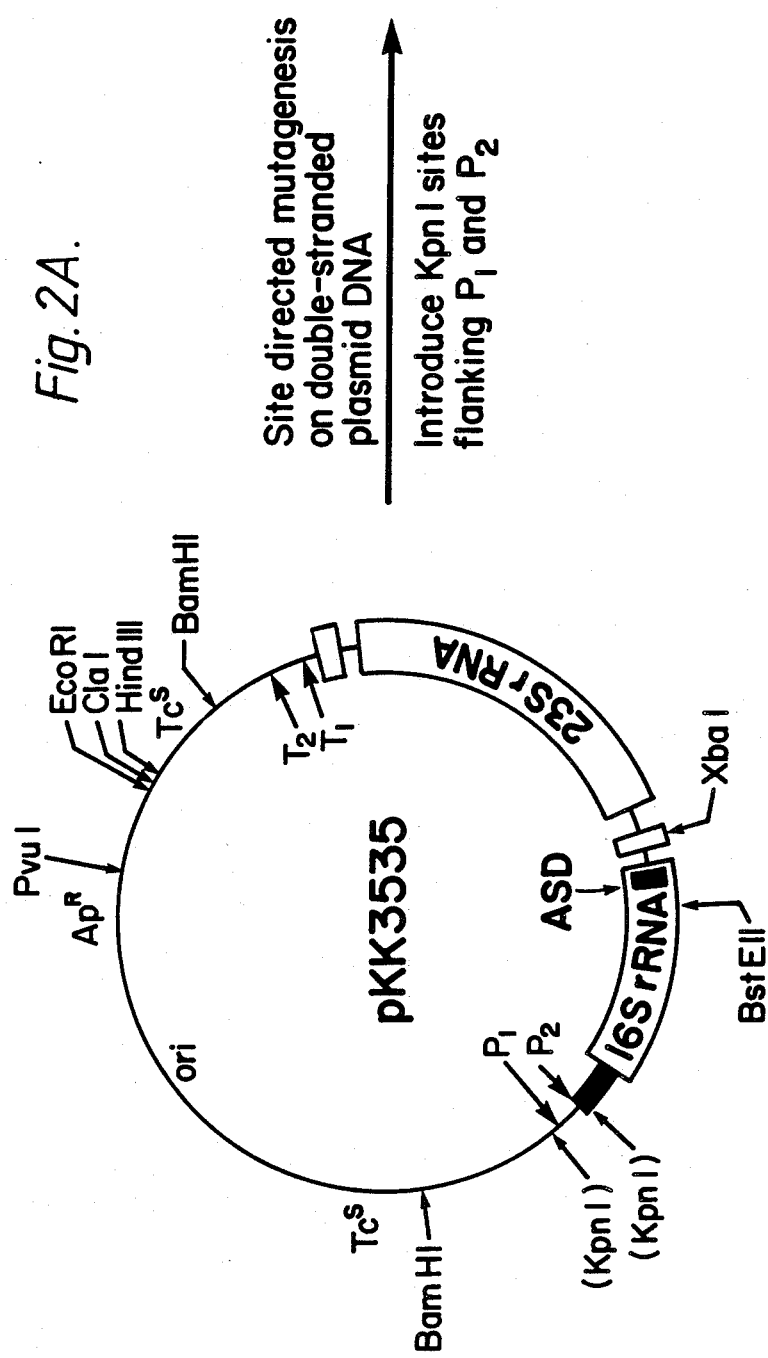
Figure 2B:
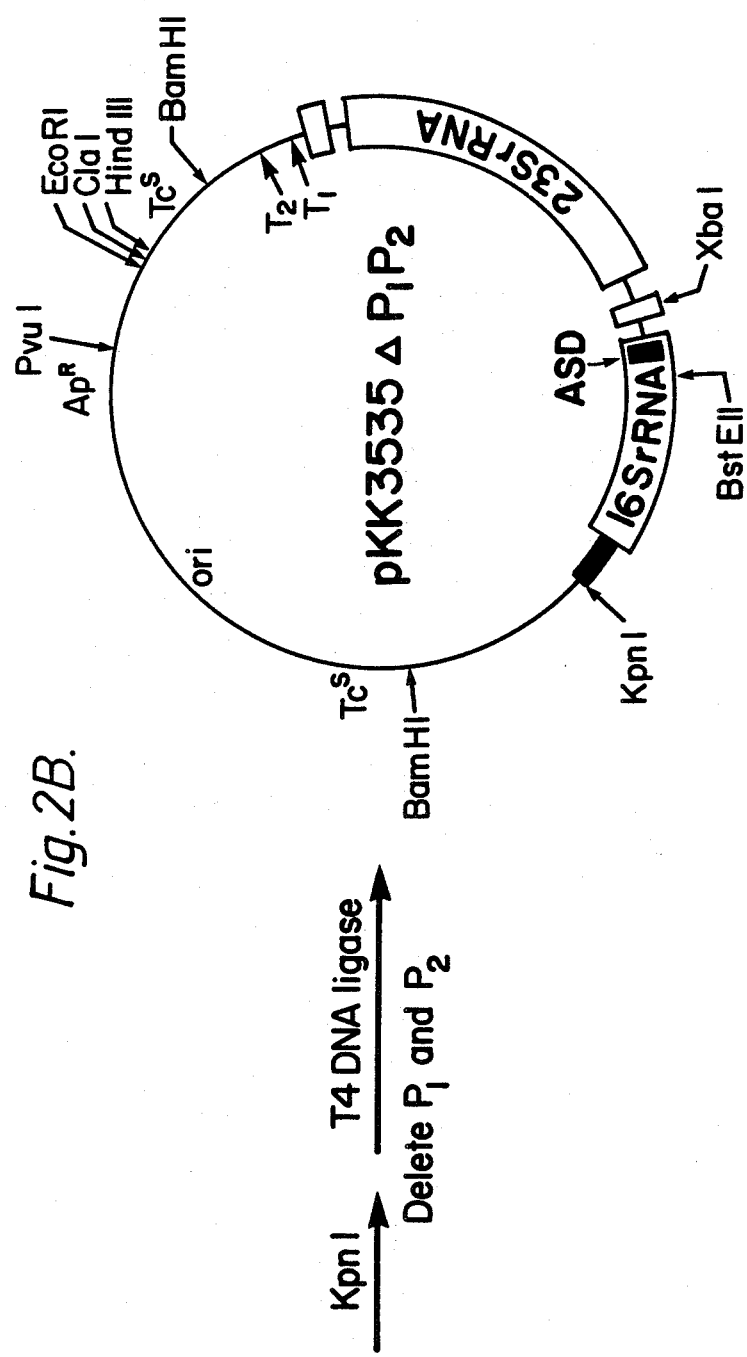
Figure 2D:
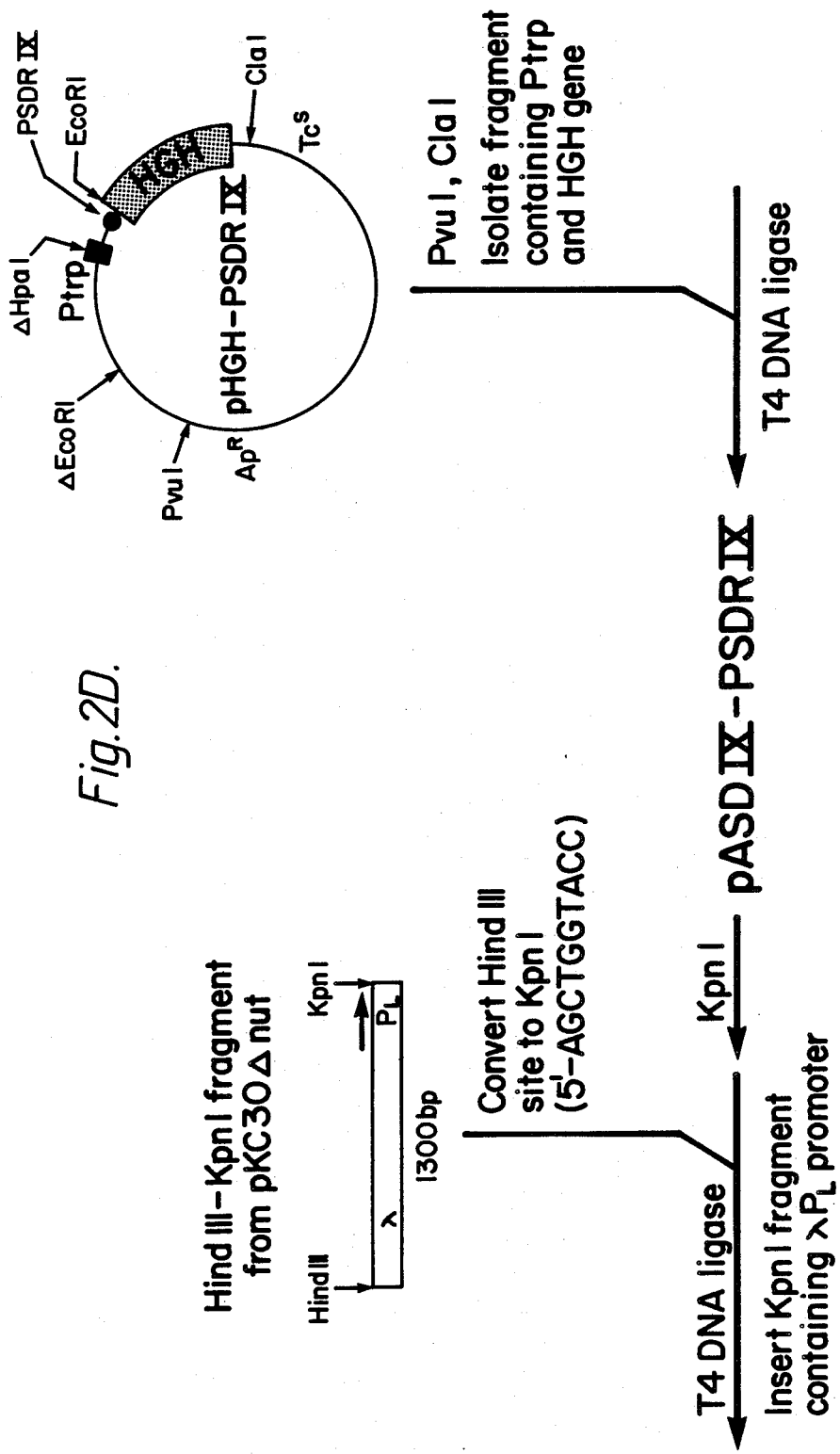
Figure 2E:
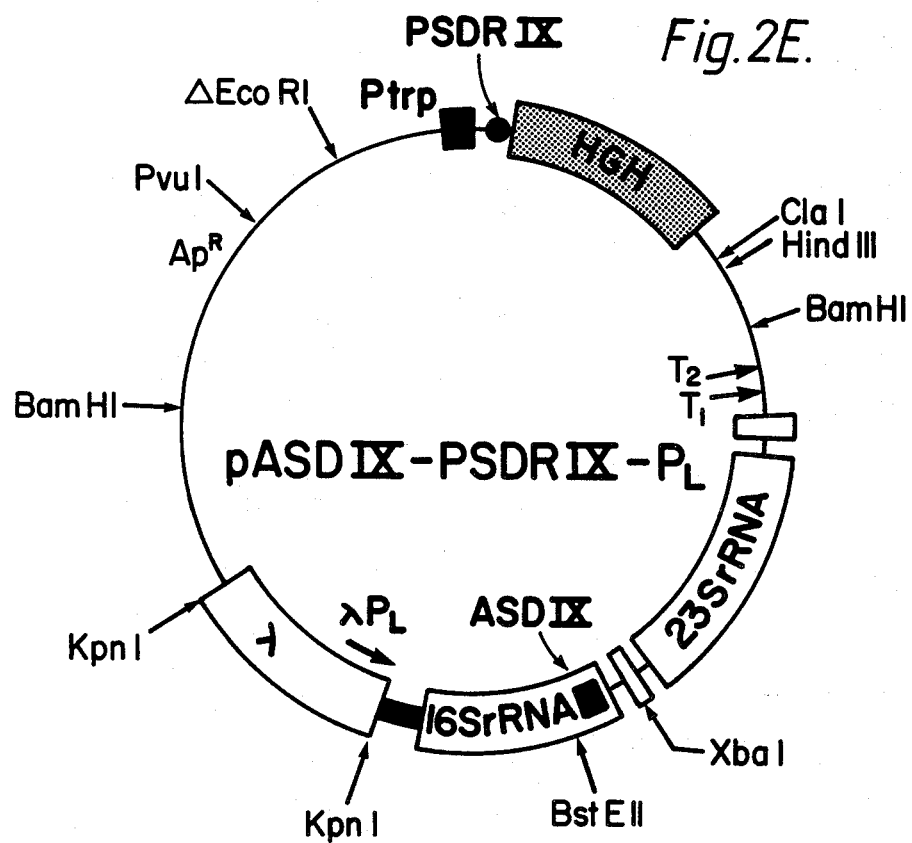

Construction of Vectors Bearing DNA Which Encodes Mutant mRNA Initiation Sequences This construction is depicted in FIG. 1. pHGH207-1*, a pBR322 derivative having a single EcoRI site and bearing DNA encoding human growth hormone (HGH) under the control of the trp promoter (Gray et al., 1984), "Biotechnology" 2: 161-165 and de Boer et al., 1982, *From Gene to Protein: Translation into Biotechnology; Miami Winter Symposia*, 19:309-327) was digested sequentially with HpaI and EcoRI. HpaI cleaves proximal of the SD region within the Pribnow Box and EcoRI cuts immediately before the HGH start codon, resulting in two vector fragments. The large vector fragment is recovered. This fragment is devoid of the trp SD sequence.

Oligonucleotide PSDR-IX was prepared synthetically in vitro and inserted using T4 DNA ligase in the same fashion as has been described previously (de Boer et al., 1983, "DNA" 2(3): 231-235 and de Boer et al., 1983, "Biochem Soc. Symp." 48: 233-244). The sequence for PSDR-IX is described in FIG. 1. It contains a 5' blunt end for ligation to the vector HpaI cut blunt end and a 3' cohesive EcoRI terminus. PSDR-IX contains a mutant mRNA SD sequence (CCTCC) which is transcribed as CCUCC, thus being the same as (and therefore not complementary to) the consensus *E. coli* rRNA ASD sequence. The ligation mixture was used to transform *E. coli* 294 (ATCC 31446). . Plasmid DNA was recovered from an amp$^r$ colony and digested with BamHI to linearize the plasmid. A BamHI-ClaI converter was ligated to the digested plasmid as shown in FIG. 1 and the ligation mixture used to transform *E. coli* 294. The purpose of this step was to convert the BamHI site to a ClaI site. pHGH-PSDR-IX was recovered from an amp$^r$ colony and its sequence confirmed to be as shown in FIG. 1. This sequence contained a modified trp promoter Pribnow Box (double overline), the deleted HpaI site (ΔHpaI), the transcriptional start site (+1), and sequences from the starting plasmid (lower case nucleotides).

The foregoing procedure was repeated with PSDR-X. Here the mutant mRNA SD sequence GTGTG was a less radical departure from the consensus GGAGG SD sequence than the CCTCC sequence in PSDR-IX.

Obviously, the same procedure can be used to generate a large bank of mutants in which the SD sequence, its spatial placement with respect to the start codon and/or the nucleotides in the SD flanking regions are varied by simply preparing different synthetic fragments.

EXAMPLE 2

Construction of Vector Bearing DNA Encoding Complementary Mutant 16S rRNA

Plasmid pKK3535 is prepared in accord with known procedures (Brosius et al., 1981, "J. Mol. Biol." 148: 107-127 and Brosius et al., 1981, "Plasmid" 6: 112-118). This plasmid is depicted in FIG. 2 of the latter reference and FIG. 2 herein. It contains the rrnB rRNA operon (encoding 16S and 23S rRNA) in a pBR322 vector under the control of tandem P1 and P2 rRNA promoters. The rrnB ribosomal RNA operon is obtained from the E. coli genome. In FIG. 2, the black region denominated "ASD" is the target anti-SD sequence found at the 3' end of the rRNA transcript. The RNA encoded by the black region 5' to the 16S rRNA is processed from the 16S rRNA after transcription. T1 and T2 are transcription terminator regions. For the purposes herein, the starting plasmid should encode the preprocessed form of the 16S rRNA and have a transcription terminator recognized by E. coli. The parenthetical Kpn sites are added in the following procedure.

Plasmid pKK3535 was treated using the heteroduplex mutagenesis process of Morinaga et al. ("Biotechnology", July 1984, pp 636-639) in order to remove an approximately 100 bp fragment containing the P1 and P2 tandem promoters. This was the first step in substituting an inducible promoter for the constitutive P1 and P2 promoters. One approximately 1 μg aliquot of pKK3535 was digested with ClaI and PvuI. A second approximately 1 μg aliquot was digested with PstI and partially with HindIII. Cut plasmid from each digestion mixture was isolated, the plasmid fragments were mixed, DNA duplexes were denatured by heating for 3 min. at 100° C., and the following synthetic oligonucleotide primers were added:

Kpn P1:
```
  1216                                        1191
                     KpnI
5'P—TTATAGGGAGGGTACCCGGCCTGACA—OH
```

Kpn P2:
```
  1364                                        1339
                     KpnI
5'P—CGCTTTTTCTGGTACCCGCGGGGTGT—OH
```

The numbers indicate the corresponding positions in rrnB of pKK3535 as given by Brosius et al. (op cit). The reaction mixture was slowly cooled to 4° C. and T4 DNA ligase (100 units), the large fragment of E. coli DNA polymerase (5 units), and all four deoxynucleotides (0.05 mM final concentration) were added. The sample was incubated overnight at 12.5° C. E. coli 294 was transfected with the incubated sample and plasmid DNA with the desired structure was isolated from an amp$^r$ colony. This plasmid contained KpnI sites flanking P1 and P2 as shown in FIG. 2. This plasmid was digested with KpnI, the large fragment isolated and ligated in order to recircularize the plasmid. Plasmid pKK3535ΔP1P2 was recovered wherein the P promoters were deleted.

The next steps have as their objective the introduction of mutant ASD regions which are complementary to the PSDR-IX or PSDR-X sequences in Example 1. One approximately 1 μg aliquot of plasmid pKK3535ΔP1P2 was digested with BstEII and XbaI, while a second was digested with PvuI and ClaI, the cut plasmid from each digestion mixture isolated, the fragments were combined, and the duplexes were heat denatured at 100° C. for 3 min. and reannealed in the presence of the following synthetic oligonucleotide primer:

```
3CGCCAACCTAGTCCTCCAATGGAATTTCT
``` wherein the dots indicate bases complementary to the 3' region of the DNA encoding the wild-type 16S rRNA. The transcription of this DNA encoding the 3' end of the modified 16S rRNA gene in pKK3535ΔP1P2AS-DIX yields rRNA containing the following sequence:

```
5'AGGGGGAACCUGCGGUUGGAUCAG-
    GAGGUUA-OH
```

Accordingly the ASDIX sequence is the complement to the normal ASD sequence CCUCC, which was installed in the mutant pHGH-PSDR-IX plasmid in Example 1.

The foregoing procedure is repeated using the following mutagenesis primer:

```
3'CGCCAACCTAGTGTGTGAATG-
    GAATTTCT
``` denominated ASDX. The rRNA transcribed from the resulting pKK3535ΔP1P2ASDX includes the sequence:

```
5'AGGGGAACCUGCGGUUG-
    GAUCACACACUUACC-OH
``` wherein the CACAC region is the complement to the mutant mRNA transcribed from pHGH-PSDRX in Example 1.

Another mutant DNA encoding 16S rRNA having the ASD 5'CAUAC (differing from ASDX by one base) was obtained in the same fashion. This mutant was denominated pKK3535ΔP1P2ASDXI. None of these plasmids express the 16S rRNA so they are not lethal and can be stably maintained in E. coli.

Any one of pKK3535ΔP1P2ASDX, XI or IX was treated as follows. For convenience, the latter shall be described and is depicted in FIG. 2. Plasmid pKK3535ΔP1P2ASDIX was digested simultaneously with PvuI and ClaI and the large vector fragment recovered.

pHGH-PSDRIX was digested simultaneously with PvuI and ClaI and the approximately 1800 bp vector fragment containing the trp promoter and HGH gene isolated. This fragment was ligated to the large vector fragment obtained in the preceding paragraph, the ligation mixture used to transform E. coli 294 and pASDIX-PSDRIX was recovered from an amp$^r$ colony.

pkC30Δnut (also referred to as pN02678, Gourse et al., 1985, "Proc. Nat. Acad. Sci. USA" 82: 1069-1073) is a pBR322 derivative bearing the λ PL operon which is free of the λ phage nutL sequence. Plasmid pkC30Δnut was digested simultaneously with HindIII and KpuI and the approximately 1300 bp fragment containing the λ phage PL promoter operator was recovered (the DNA sequence of the λ phage which includes this fragment is described in Hendrix et al., Lambda II, pp. 619-623, Cold Spring Harbor Laboratory, 1983, extending from about bases 35580 to about 36880). The HindIII site was converted to KpnI by ligating the 1300 bp λ PL fragment to the synthetic oligonucleotide

```
5' AGCTGGTACC
    CCATGGTCGA 5'
```

This oligonucleotide was not phosphorylated (Kinased) as the converter is self complementary; phosphate is supplied by the vector cohesive end, and only the top strand ligates. The residual gap between the bottom strand and the vector upon ligation as described below is filled in vivo.

The converted 1300 bp fragment was ligated to KpnI digested pASDIX-PSDRIX, transfected into *E. coli* K5637 (cI857) and grown at 30° C. Plasmids from amp$^r$ colonies were isolated and analyzed by restriction enzyme analysis using BglII and HindIII to identify plasmid pASDIX-pSDRIX-PL having the λ PL promoter in the correct (forward) orientation. *E. coli* K5637 (cI857) is a derivative of *E. coli* w3110 (ATCC 27325) having the phenotype λC$^{I857}$ΔBam Cro$^{27}$ Oam$^{29}$ prepared in conventional fashion. Its relevant element is a defective λ prophage (genomic insert) containing the temperature-sensitive cI857 allele of the λ repressor gene. The λ cI857 repressor is a protein that at 30° C. almost completely represses transcription under the control of the λ PL promoter. However, λ cI857 is inactivated at 42° C., so that λ PL is derepressed in cultures incubated at these temperatures. Other host cells containing the λ lysogen with the cI857 allele are satisfactory, e.g. C600λ described by Gourse et al. (op cit).

Aside from pASDIX-PSDRIX-PL and pASDX-PSDRX-PL, a plasmid pASDXI-PSDRX-PL was obtained in the same way as described above. Here, the 16S rRNA ASD mutant will complement the mRNA SD mutant, but the complementarity is not the result of perfect base pairing.

EXAMPLE 3

HGH Synthesis Using Dedicated Ribosomes

HGH was synthesized by *E. coli* K5637 transformed with pASDIX-PSDRIX-PL, pASDX-PSDRX-PL, pASDXI-PSDRX-PL and control plasmids using the following procedure. About 10 ng of plasmid DNA was added to transform competent cells of *E. coli* K5637 (CI857) or any other equivalent strain using standard procedures. Amp$^r$ transformants were obtained and grown overnight in Mg medium at 30° C. After 16 hours fresh medium was inoculated to an OD$_{551}$ cm of 0.05 in the same medium at 30° C. After 1 hour the temperature was raised to 42° C. 1 ml cell samples were taken, the cells were spun down, lysed and their hGH content was measured using a standard assay based on immunological methods.

A plasmid pASDX-PSDRX obtained in Example 2 having the incorrect orientation of the λ PL promoter was used as a negative control; mutant 16S rRNA made by transformants with this plasmid is essentially unrecognized by the wild type host cell ribosomes. Similarly, the transcripts of pHGH-PSDRX (Example 1) are unrecognized by the host cell and thus serve as an additional negative control.

Three positive controls were employed. These were pHGH 207-1 to serve, in effect, as a commercial control, pHGH 207-1 ASDwt.PL and pHGH 207-1 ASDwt. Plasmid pHGH 207-1 ASDwT-PL was made in the same fashion as pASDIX-PSDRIX-PL except that the 16S rRNA encoded the wild type ASD sequence (CCUCC) rather than ASDIX. Plasmid pHGH 207-1 ASDwt was identical to pHGH 207-1 ASDwt-PL except that the λ PL promoter had not been inserted. These three positive controls were expected to result in HGH synthesis because the transfected plasmids contain the trp promoted wild type HGH gene, resulting in transcripts recognized by normal host cell ribosomes, but not to result in the generation of dedicated ribosomes.

Figure 3:
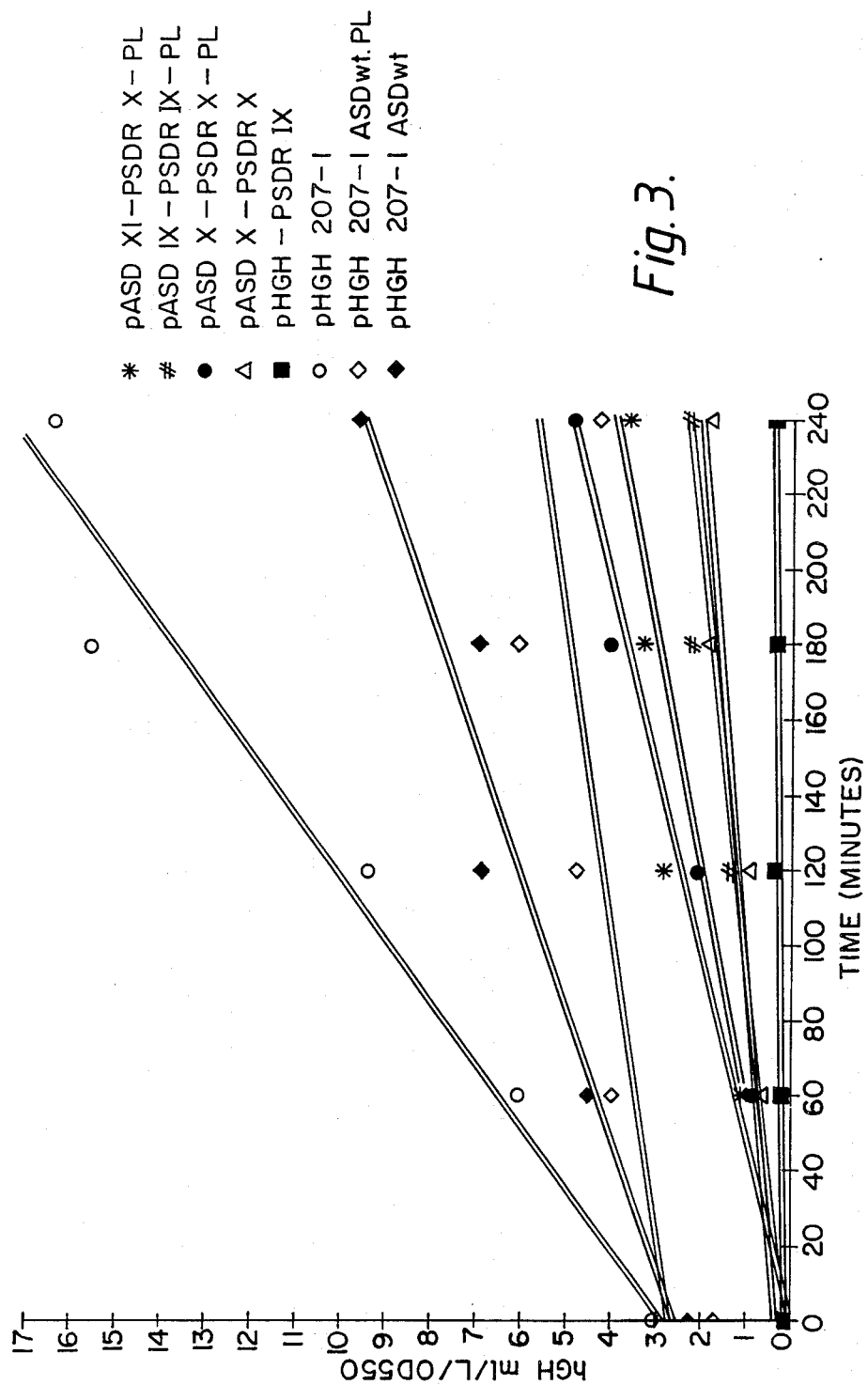
FIG. 3 is a graph showing the synthesis of human growth hormone (HGH) by transformants with the vectors of FIG. 2. It shows that dedicated ribosomes are synthesized in transformants and that they are active in producing the target protein.

The results are depicted in FIG. 3. As expected, PASDX-PSDRX and pHGH-PSDRX generated substantially no HGH since the mutant SD was unrecognized by the host cell ribosomes and mutant 16S rRNA was unpromoted or its encoding DNA was completely absent.

It is believed that pHGH 207-1 ASDwt-PL, containing the 16S rRNA wild type ASD under the control of the PL promoter, resulted in less HGH than pHGH 2071-ASDwt or pHGH 207-1 because of the presence of the operative, strong PL operator and the large size of the vector. Typically, the presence of a strong vector promoter and a large vector leads to a relatively lower vector copy number per cell, and accordingly to a lowered synthesis of product. Nonetheless, since all three plasmids contain DNA encoding HGH and the consensus SD sequence under the control of the trp promoter, it was expected that HGH would be synthesized prior to induction of λPL.

Study of the results for the plasmids bearing complementary or substantially complementary mutant SD-ASD encoding sequences demonstrates that dedicated ribosomes are produced and that the dedicated system is effective in the synthesis of protein. Even after 300 minutes the amount of HGH is continuing to increase, while the amount of HGH synthesized from conventional plasmids using endogenous ribosomes has reached a stationary level. Further refinements of the method herein, including optimizing the location and sequence of the mutant SD-ASD system as well as increasing the culture period, are expected to result in further improvements in protein synthesis.

I claim:

1. DNA encoding bacterial ribosomal 16S RNA having and introduced mutation within the last about 20 nucleotides at the 3' end of said RNA.

2. DNA encoding bacterial ribosomal 16S RNA, said RNS mutated at the 3' terminus to have the sequence GGA(N)$_a$Y(N)$_b$-OH, wherein N is a ribonucleotide, a is an integer of 0 to about 5, b is an integer of 0 to about 10 and Y is an oligoribonucleotide other than CCUCC containing about from 3 to 15 nucleotides.

3. The DNA of claim 2 wherein (N)$_a$ is UCA.

4. The DNA of claim 2 wherein (N)$_b$ is UUA, UUUCUA or UUU.

5. The DNA of claim 2 wherein Y contains greater than about 25 mole percent guanine nucleotide.

6. The DNA of claim 2 wherein Y is GGAGG, CACAC, or CAUAC.

7. A mutual ribosome comprising the RNA encoded by the DNA of claim 1.

8. A mutated ribosome comprising the RNA encoded by the DNA of claim 2.

9. A bacterial cell comprising the ribosome of claim 7.

10. A bacterial cell comprising the ribosome of claim 8.

11. The mutated ribosome of claim 7 which is substantially incapable of translating mRNA endogenous to a host cell as compared to the capability of the non-mutated ribosomes.

12. The ribosome of claim 8 which is substantially incapable of translating mRNA endogenous to a host cell as compared to the capability of the non-mutated ribosomes.

13. The cell of claim 11 which is transfected with DNA encoding an mRNA containing a Shine-Dalgarno sequence which is complementary to oligoribonucleotide Y.

14. The cell of claim 12 which is transfected with DNA encoding an mRNA containing a Shine-Dalgarno sequence which is complementary to oligoribonucleotide Y.

15. DNA encoding mRNA, said mRNA having a Shine-Dalgarno sequence which contains greater than about 25 mole percent cytosine nucleotide.

16. The DNA of claim 15 wherein the sequence is CCUCC.

17. A method for producing protein in cell culture comprising (1) providing at least one vector comprising (a) a DNA sequence encoding bacterial 16S rRNA having a mutant ASD sequence; and (b) a DNA sequence encoding a protein and having an untranslated 5' region comprising a mutant SD sequence which is complementary to the mutant 16S rRNA ASD sequence;

(2) transfecting the vector into a host cell; and (3) culturing the host cell to permit expression of the protein.

18. The method of claim 17 wherein the DNA sequences encoding the 16S rRNA and protein are located on the same vector.

19. The method of claim 17 wherein the DNA sequence encoding the 16S rRNA is under the control of an inducible promoter.

20. The method of claim 19 wherein the protein is a eukaryotic protein.

21. The method of claim 20 wherein the protein is a mammalian protein.

* * * * *